United States Patent
Mohajer-Shojaee

(10) Patent No.: US 10,420,585 B2
(45) Date of Patent: Sep. 24, 2019

(54) LAPAROSCOPIC CANNULA WITH SUTURING PASSAGE CUTOFF

(71) Applicant: Reza Mohajer-Shojaee, Encino, CA (US)

(72) Inventor: Reza Mohajer-Shojaee, Encino, CA (US)

(*) Notice: Subject to any disclaimer, the term of this patent is extended or adjusted under 35 U.S.C. 154(b) by 260 days.

(21) Appl. No.: 15/366,552

(22) Filed: Dec. 1, 2016

(65) Prior Publication Data

US 2017/0079639 A1  Mar. 23, 2017

Related U.S. Application Data

(63) Continuation-in-part of application No. 14/710,669, filed on May 13, 2015, now Pat. No. 9,636,104,
(Continued)

(51) Int. Cl.
| | |
|---|---|
| *A61B 17/34* | (2006.01) |
| *A61B 17/02* | (2006.01) |
| *A61B 17/04* | (2006.01) |
| *A61B 17/00* | (2006.01) |
| *A61M 13/00* | (2006.01) |

(52) U.S. Cl.
CPC ...... *A61B 17/3423* (2013.01); *A61B 17/0057* (2013.01); *A61B 17/02* (2013.01); *A61B 17/0218* (2013.01); *A61B 17/0482* (2013.01); *A61B 17/0485* (2013.01); *A61B 17/3421* (2013.01); *A61B 17/3474* (2013.01); *A61B 2017/00637* (2013.01); *A61B 2017/00663* (2013.01); *A61B 2017/347* (2013.01); *A61B 2017/3445* (2013.01);
(Continued)

(58) Field of Classification Search
CPC . A61B 17/3421; A61B 17/3423; A61B 17/02; A61B 17/0218; A61B 17/0482; A61M 13/003
USPC ........................ 600/201–210, 215, 235, 213; 604/167.01–167.06, 158–161
See application file for complete search history.

(56) References Cited

U.S. PATENT DOCUMENTS

| 4,585,440 A | 4/1986 | Tchervenkov et al. |
|---|---|---|
| 4,673,393 A | 6/1987 | Suzuki et al. |

(Continued)

FOREIGN PATENT DOCUMENTS

EP  1219253 A1  7/2002

OTHER PUBLICATIONS

International Search Report—International Application No. PCT/US2012/025373.

*Primary Examiner* — Zade Coley
*Assistant Examiner* — Amy R Sipp
(74) *Attorney, Agent, or Firm* — Dinsmore & Shohl LLP

(57) ABSTRACT

A cannula for use in laparoscopic surgery has a central passage which may accept a trocar to create a laparoscopic incision in a body wall to an inner body cavity. A tubular section of the cannula is then pressed into the incision to form a port. The tubular section has passages through its walls for suturing needles and a source for insufflating gas. A tubular sleeve is slidably supported on the exterior surface of the tubular cannula for movement between a raised position clear of the needle passage exit ports and a lowered or rotated position blocking the exit ports to prevent insufflation gases from passing into the body wall.

20 Claims, 12 Drawing Sheets

Related U.S. Application Data which is a continuation-in-part of application No. 13/984,240, filed as application No. PCT/US2012/025373 on Feb. 6, 2012, now Pat. No. 9,033,872.

(60) Provisional application No. 61/443,286, filed on Feb. 16, 2011.

(52) U.S. Cl.
CPC ............... *A61B 2017/3449* (2013.01); *A61B 2017/3484* (2013.01); *A61M 13/003* (2013.01)

(56) References Cited

U.S. PATENT DOCUMENTS

| | | | |
|---|---|---|---|
| 5,300,035 A | 4/1994 | Clement | |
| 5,364,410 A | 11/1994 | Failla et al. | |
| 5,507,758 A | 4/1996 | Thomason et al. | |
| 5,716,369 A * | 2/1998 | Riza | A61B 17/0469 606/139 |
| 5,954,734 A | 9/1999 | Thomason et al. | |
| 5,984,948 A * | 11/1999 | Hasson | A61B 17/0057 606/144 |
| 5,993,471 A * | 11/1999 | Riza | A61B 17/3498 606/185 |
| 8,206,294 B2 | 6/2012 | Widenhouse et al. | |
| 8,808,248 B2 | 8/2014 | Schultz | |
| 2005/0070851 A1 | 3/2005 | Thompson et al. | |
| 2005/0096507 A1* | 5/2005 | Prosek | A61B 17/34 600/204 |
| 2008/0097485 A1 | 4/2008 | Shpaichler et al. | |
| 2008/0132847 A1 | 6/2008 | Wing et al. | |
| 2008/0255519 A1 | 10/2008 | Piskun et al. | |
| 2009/0012447 A1 | 1/2009 | Huitt et al. | |
| 2010/0002958 A1 | 1/2010 | Wu | |
| 2010/0022958 A1 | 1/2010 | Moreno, Jr. et al. | |
| 2010/0081881 A1 | 4/2010 | Murray et al. | |
| 2010/0228198 A1 | 9/2010 | Widenhouse et al. | |
| 2010/0240959 A1 | 9/2010 | Donahue | |
| 2010/0249810 A1* | 9/2010 | Taylor | A61B 17/3421 606/148 |
| 2010/0256567 A1 | 10/2010 | Smith | |
| 2010/0274093 A1 | 10/2010 | Shelton, IV | |
| 2011/0112370 A1 | 5/2011 | Nguyen et al. | |
| 2011/0218568 A1 | 9/2011 | Voss | |
| 2012/0010471 A1 | 1/2012 | Mire et al. | |
| 2012/0035623 A1 | 2/2012 | Bagaoisan et al. | |
| 2014/0171981 A1* | 6/2014 | Jimenez | A61B 17/0057 606/148 |
| 2017/0281154 A1* | 10/2017 | Hess | A61B 17/0218 |
| 2017/0281229 A1* | 10/2017 | Hess | A61B 17/0218 |

* cited by examiner

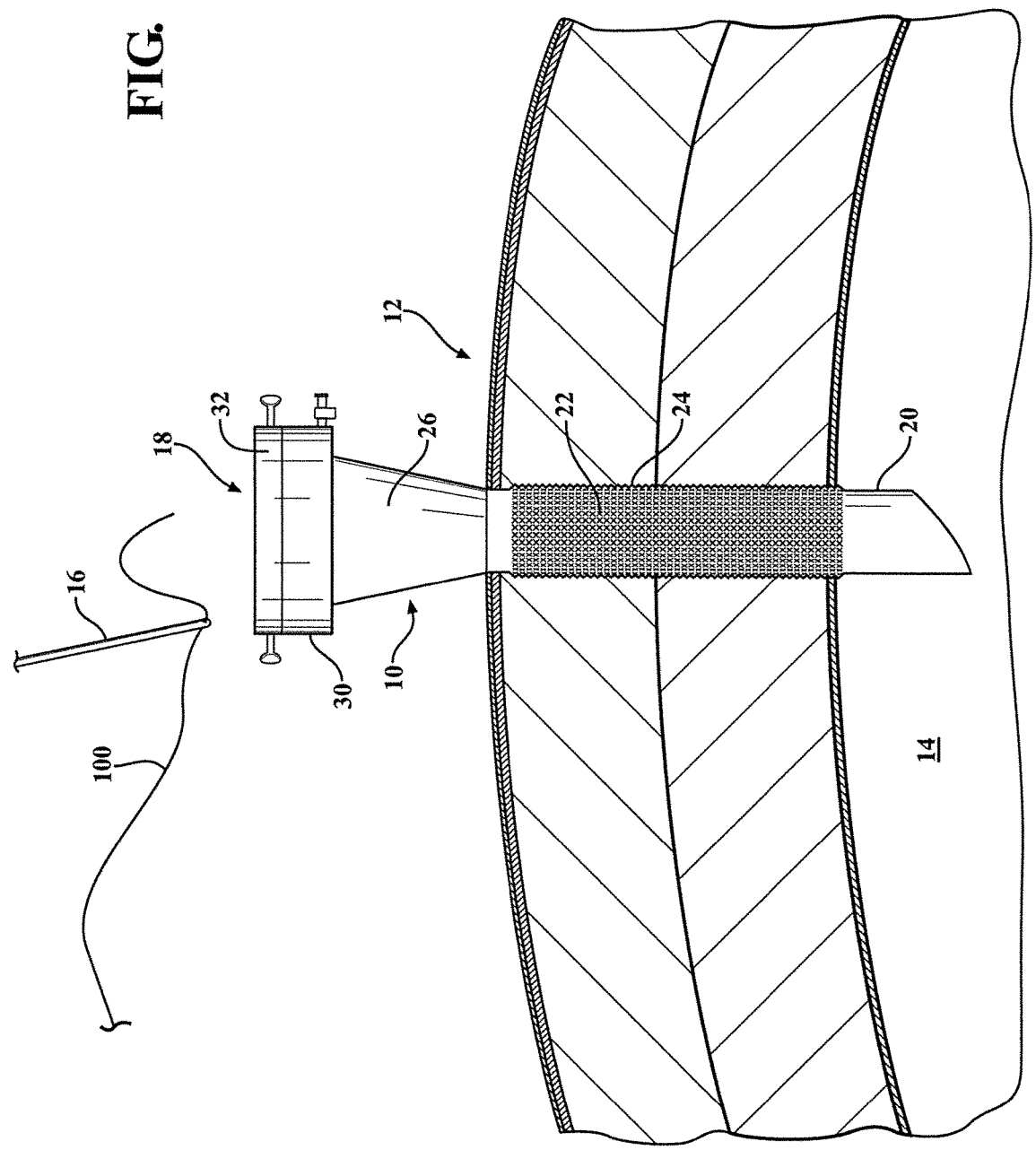

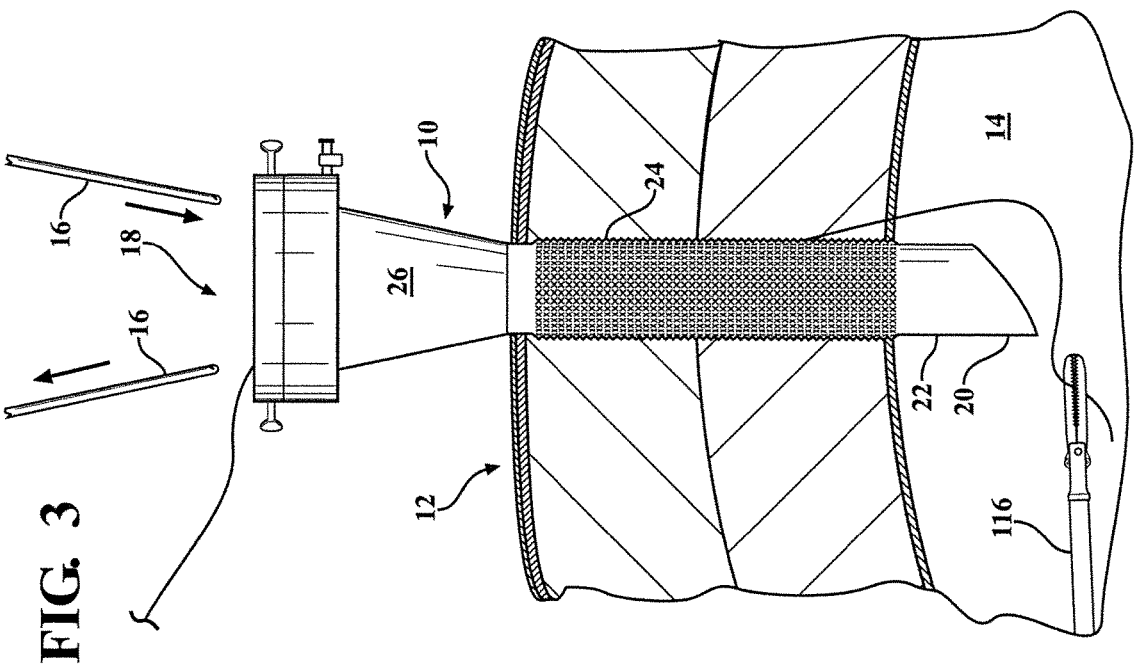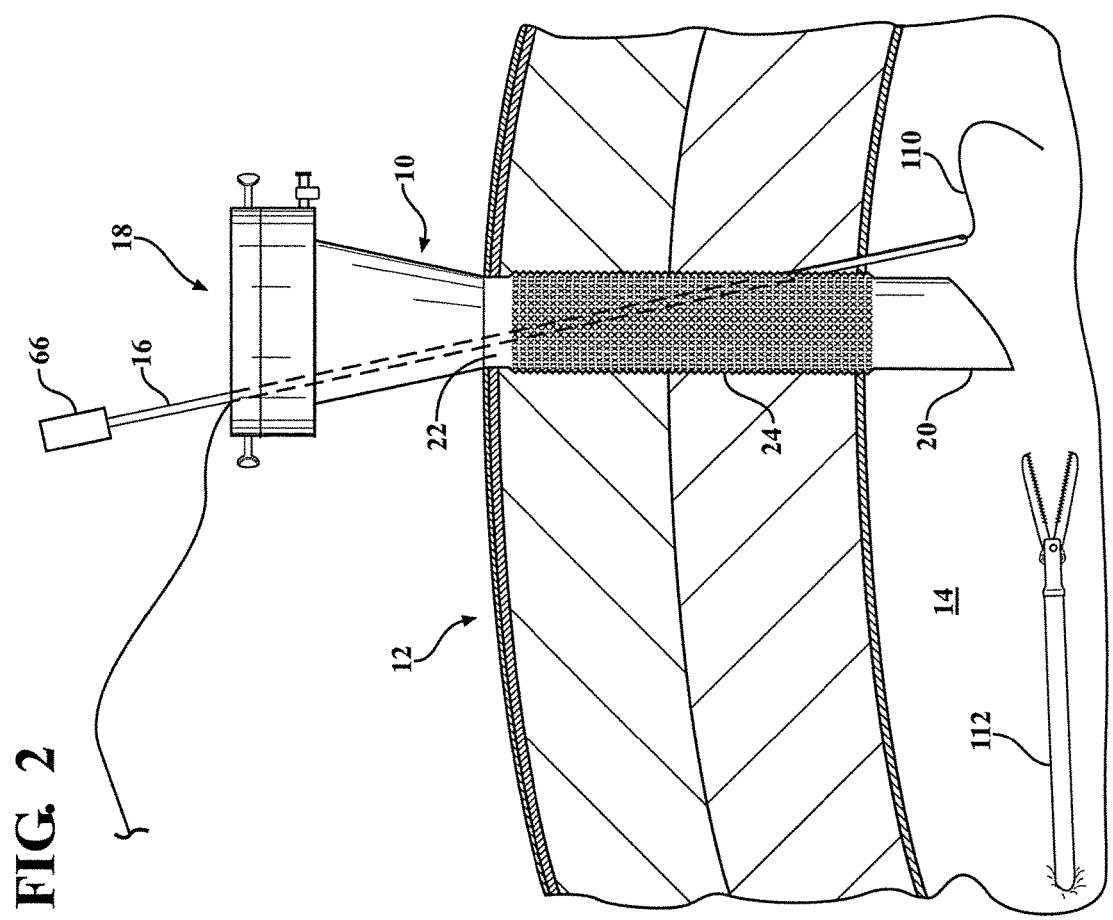

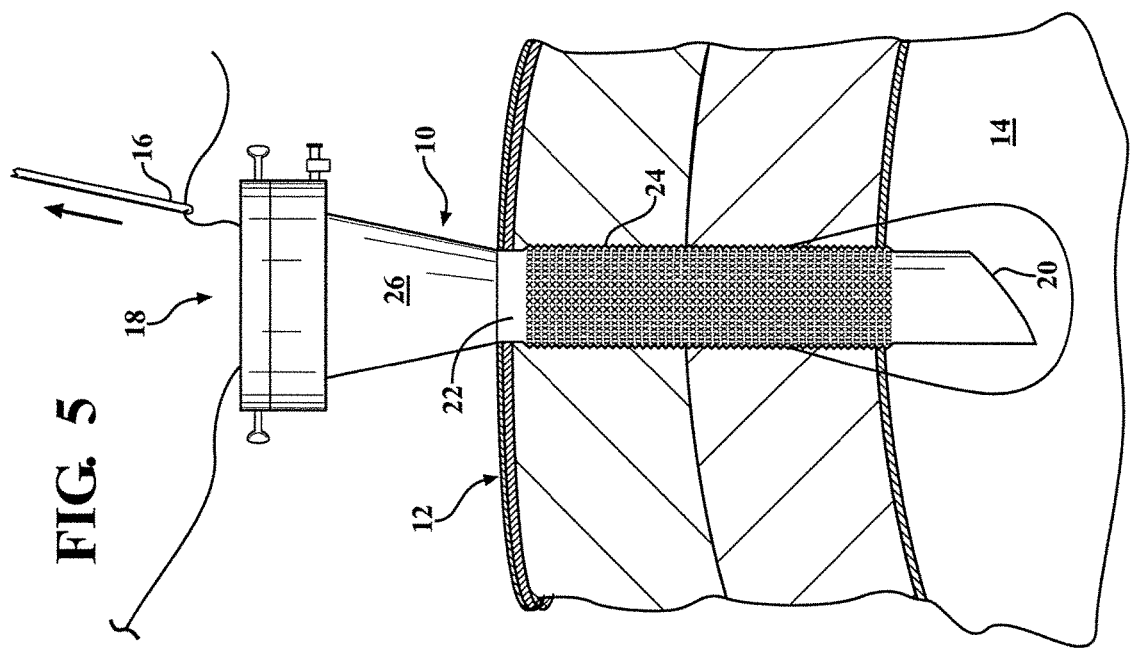
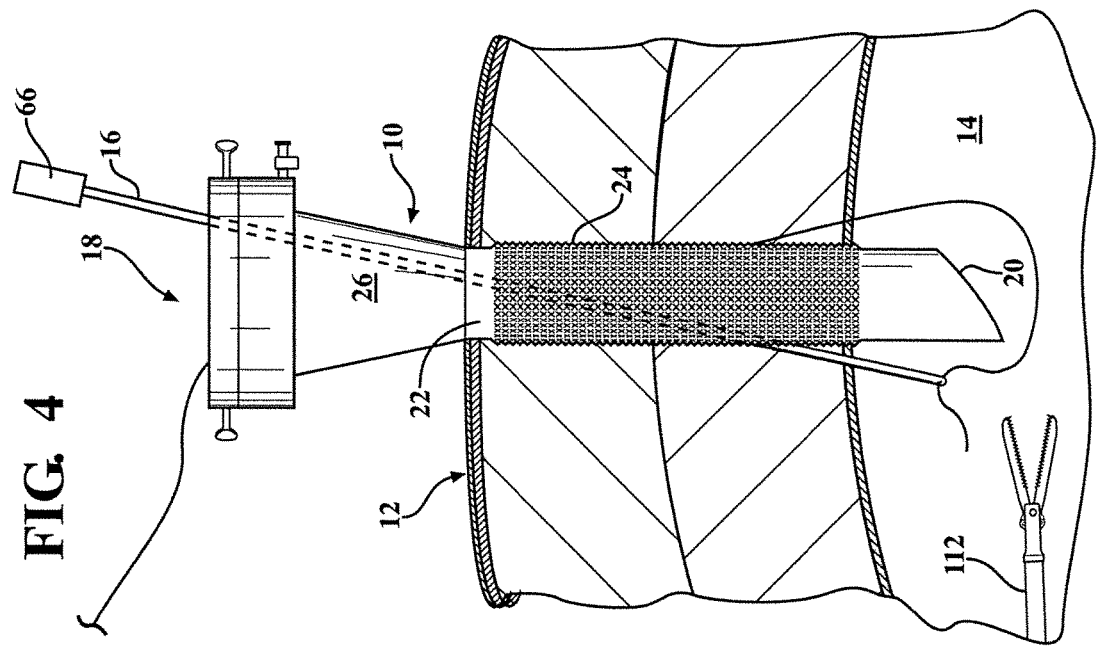

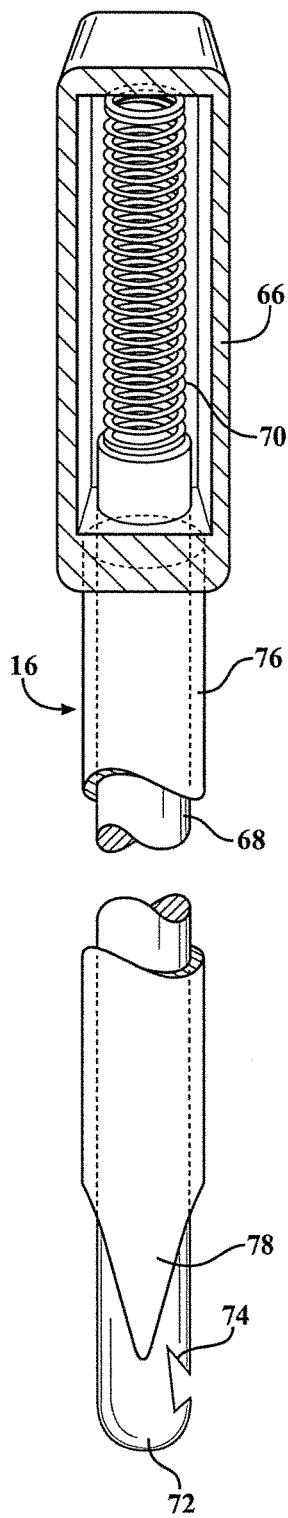
FIG. 8
FIG. 9
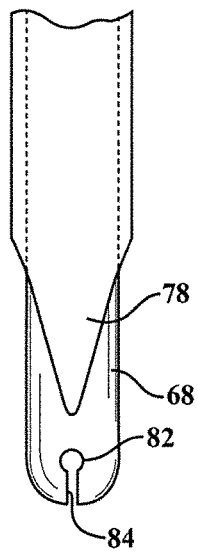
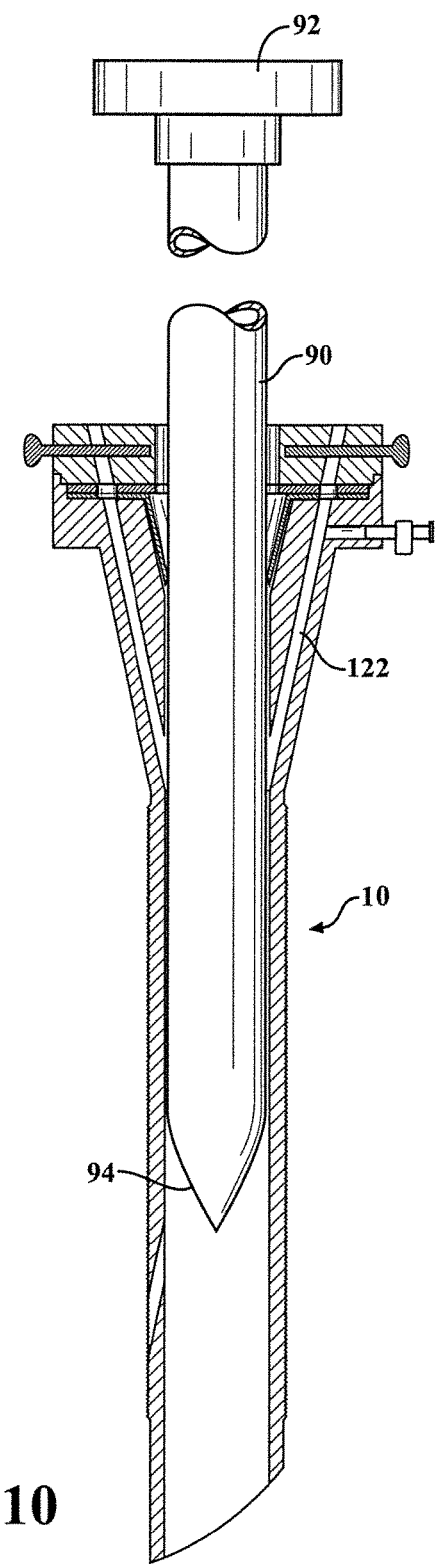
FIG. 10

LAPAROSCOPIC CANNULA WITH SUTURING PASSAGE CUTOFF

REFERENCE TO RELATED APPLICATIONS

This application is a continuation-in-part of U.S. patent application Ser. No. 14/710,669, filed May 13, 2015, which is a continuation-in-part of U.S. patent application Ser. No. 13/984,240, filed Feb. 19, 2014, now U.S. Pat. No. 9,033,872, which is the U.S. national stage of PCT/US2012/025373 filed Feb. 16, 2012, which claims priority of U.S. Provisional Patent Application No. 61/443,286 filed Feb. 16, 2011, the entire content of all of which is incorporated herein by reference.

FIELD OF THE INVENTION

This invention relates to cannulas and accessories for use in laparoscopic surgery and more particularly to a cannula enabling suturing of a laparoscopic incision while maintaining the level of insufflating gas pressure and avoiding gas penetration into the body tissue.

BACKGROUND OF THE INVENTION

In the performance of a laparoscopic operation, an incision is first made through the body wall into a body cavity typically using a trocar, an elongated tube having a three point sharpened distal end. The trocar is often supported in a cannula, a shorter tube which passes into the incision made by the trocar and lines the wall of the incision, providing a port for entry into the incision. Various laparoscopic instruments such as oculars, cameras, or instruments similar to scissors or pliers may be introduced into the incision through the cannula to perform the necessary operation. The cannula also typically includes a port for receiving gas which may be introduced into the body cavity through the incision to inflate the cavity to increase the accessibility of the surgical site.

In typical laparoscopic procedures with most existing laparoscopic instruments, in order to close the incision and suture any cuts made in the cavity, it is necessary to remove the cannula, deflating the surgical cavity, and introduce a new suture guide which may have ports for needles connected to sutures for closing the incision. Other newer suturing devices do not require the removal of the cannula in order to introduce suturing devices, in that the suturing device itself is inserted through the center of the initial cannula. These suturing devices are cost prohibitive. Accordingly, after the suture carrying cannula or the suturing device is introduced, it is typically necessary to reinsufflate the body cavity.

SUMMARY OF THE INVENTION

The present invention is directed toward a single laparoscopic tool which allows a surgeon to make an incision; enter a body cavity; inflate the cavity; perform an operation through the cannula of the tool, which serves as a port, along with other instruments inserted through additional ports; and then close the incision through the same cannula with a suture carried by one or more needles passed through passages formed through the wall of the cannula. Therefore, the entire operation from incision to suturing can be performed with a single cannula, substantially simplifying the operative process relative to previous laparoscopic techniques.

In a preferred embodiment of the invention, which will be subsequently described in detail, a generally cylindrical cannula has a laterally enlarged section at its proximal end, which end lies externally of an incision, containing one or a pair of inclined passages for receiving suture needles passing through the side walls of the cannula, where they allow the needles to enter the interior volume of the tubular section of the cannula. In the two needle version, needles inserted into these inclined passages from the proximal end cross one another, with slight lateral separation, approximately midway through the length of the tubular section of the cannula. Another pair of passages in the opposed side walls of the tubular section of the cannula are formed near the distal end and align with the two passages at the proximal end so that a suturing needle passed into the top of the cannula through one of the inclined passages extends across the width of the tubular section and can exit the cannula at one of the two distal passages.

Shortly beyond the proximal end of the cannula, each of the inclined passages passes through manually actuable valves which may be opened to allow the needles to pass through them and may be closed when the needles are removed to prevent the escape of the insufflating gases which have been passed through the cannula and into the body cavity.

A gas conduit controlled by a valve preferably feeds into one of the inclined passages at the proximal end of the cannula, when there is no needle in that passage, to allow inflation of the body cavity to provide clearance for the surgical operation. The proximal end of the tubular passage through the cannula carries a flap valve near its upper end which closes under the pressure of insufflating gases to prevent the escape of the gases through the proximal end of the cannula port.

The suturing needles used with the present invention must pass through a portion of the body wall section when they exit through the distal passages through the cannula wall so that the sutures can engage and bring together portions of the body cavity on opposed sides of the cannula in order to close off the incision. Accordingly, the suture needles must have the ability to cut through the cavity wall. The suture needles are accordingly formed with a central cylindrical section which has a blunt distal end with a suture-engaging configuration. The proximal end of the suture needle is disposed within a handle where it is engaged by a compression spring which biases the cylindrical section toward an extended position from the handle. The cylindrical section is surrounded by a sheath which has a pointed distal end capable of cutting through tissue. The proximal end of the cutting sheath is fixed to the handle. When the blunt end of the tubular section is unobstructed, the spring bias causes it to extend beyond the end of the cutting sheath. When the needle is pressed against the body wall, the blunt end of the tubular section is forced against the spring bias and the pointed end of the cutting sheath extends downwardly into the tissue so that upon further pressure on the handle of the needle it cuts through the tissue, outside of the wall of the body cavity, so that a suture carried by the distal end of the needle is within the body cavity. The free end of the suture within the body cavity is then grasped by a pliers-like tool introduced into the body cavity from another port and manipulated by the surgeon using an endoscope, introduced through still another port, to view the interior of the body cavity.

A second suturing needle is then introduced through the other cavity in the cannula so that it pierces the tissue of the body cavity at a point displaced from the point of entrance into the cavity of the first suturing needle. The pliers-like tool may be used to join the free end of the suture to the distal end of the second needle. The second needle is then pulled back through the cannula to the exterior of the body cavity where the two ends of the suture may be knotted to secure the incision.

In one alternative embodiment of the invention, the cannula has only a single inclined passage for a suture needle which is used to carry a suture into the body cavity. The free end of the suture within the body cavity may then be grasped by an instrument introduced through a second port and detached from the needle. The entire cannula may then be rotated about its central axis while in the incision so that the suture may be reinserted on the needle end and drawn through the cannula passage, allowing the two ends of the suture to be knotted to close the incision. The two passage embodiment avoids the need to rotate the cannula within the cavity which may induce bleeding from the incision.

The insufflating gas used in laparoscopic operations is typically $CO_2$ because it is so easily absorbed in the body tissues and leaves no residue. The $CO_2$ may be combined with other similarly absorbable gases. Because of the high absorbability of the $CO_2$ in body tissues, a constant supply of the gas must be fed into the body cavity during the operation to maintain insufflation of the body cavity. In situations in which the distal exit cavities of the suturing needles from the cannula are located within the abdominal wall, rather than within the cavity itself, there is a possibility of $CO_2$ in liquids seeping into the tissue under pressure, causing subcutaneous emphysemas or other undesirable side effects.

In another alternative embodiment of the invention, in order to prevent the seepage of the gases into the tissues, a blocking member in the form of a tubular sleeve is supported on the outer diameter of the cannula in such a way that it may be moved, typically manually, between a first position in which it covers the exit ports of the needle passages in the cannula to prevent the inflating gases from being introduced into the body tissue, and a second position, closer to the proximal end of the cannula, in which the blocking member sleeve does not extend over the outlet ports and allows the suturing needles to be introduced. Longitudinally extending tongues projecting from the opposed inner surfaces of the blocking member sleeve ride in longitudinal grooves formed in opposed sides of the cannula to guide the blocking member sleeve.

BRIEF DESCRIPTION OF THE DRAWINGS

Other objects, advantages, and applications of the present invention will be made apparent by the following detailed description of preferred embodiments of the invention. The description makes reference to the accompanying drawings in which:

FIGS. 1-5 all represent sections through the wall of a body cavity in which the first embodiment of the cannula of the present invention has been inserted and the sequential steps employed in performing suturing of the wall of the body cavity using the cannula and the suturing needles of the present invention;

FIG. 8 is a sectional view, partially broken away, of the suturing needle of the present invention;

FIG. 9 illustrates the cutting end of an alternative form of suturing needle;

FIG. 10 is a cross-sectional view of the first embodiment of the cannula of the present invention with a trocar inserted into the barrel of the cannula;

DETAILED DESCRIPTION OF THE INVENTION

Figure 6:
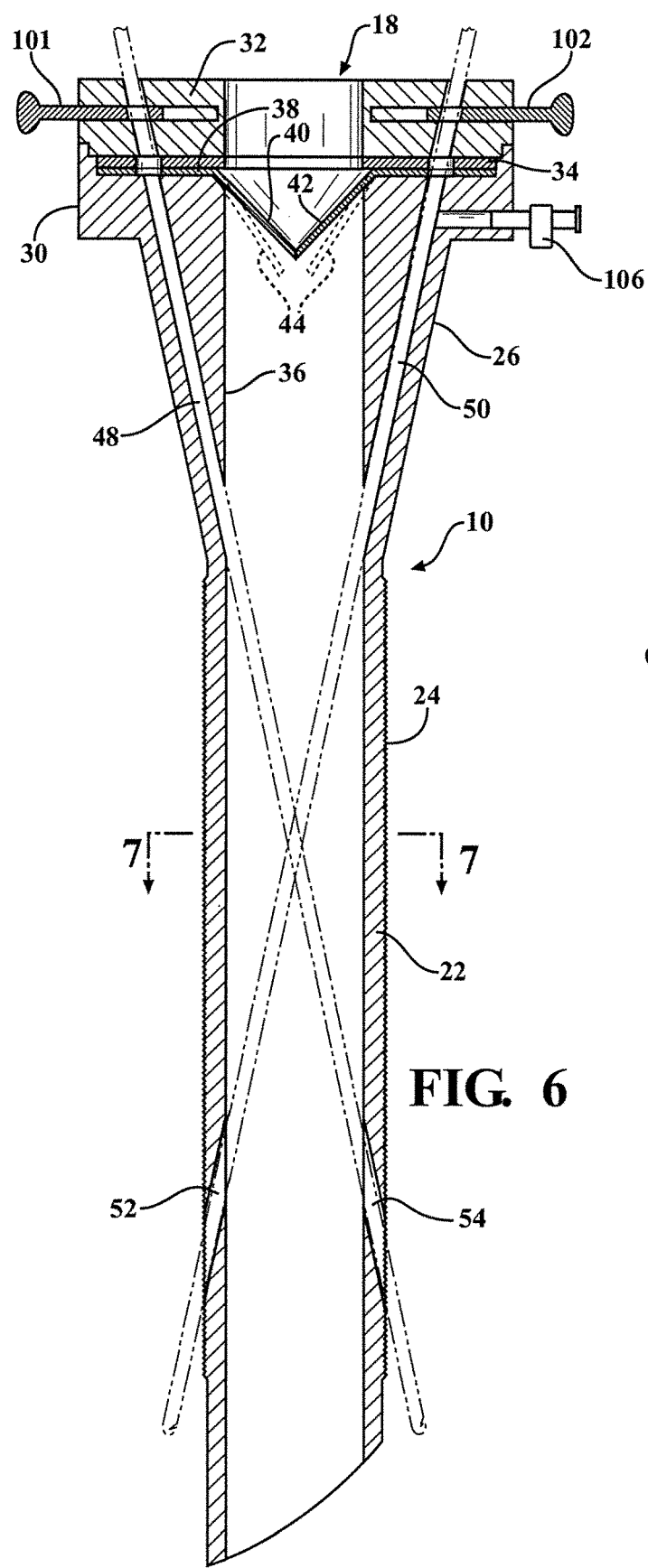
FIG. 6 is a cross-sectional view of the cannula of the present invention illustrating the paths of the two suturing needles in phantom lines.

FIGS. 1-5 illustrate a first embodiment of a cannula, generally indicated at 10, disposed in an operating position within a wall, generally indicated at 12, of a body cavity 14. These drawings illustrate the sequence of operations in utilizing the cannula 10 and a pair of suture needles 16 to close the incision in the body wall 12 required to position the cannula 10 with its proximal end 18 externally of the body cavity and its distal end 20 within the body cavity.

Figure 7:
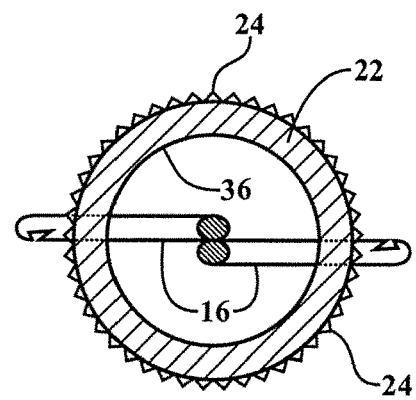
FIG. 7 is a cross section through the drawing of FIG. 6, taken along line 7-7, illustrating the relationship of the two suturing needles as they pass through the barrel of the cannula.

The cannula 10, illustrated in cross section in FIGS. 6 and 7, includes a tubular section 22 of somewhat greater length than the body wall 12 so it may extend through the body wall with its lower end 20 in the underlying body cavity 14. The tubular section 22 is formed with serrations 24 on its surface to firmly secure it within the body wall 12.

At the proximal end of the cannula 10 the side walls of the cannula flare outwardly in a section 26 so that the width of the cannula on the proximal side of the tubular section 24 has a greater width than the balance of the tubular section.

At the extreme proximal end of the cannula 10 the walls extend laterally in a section 30 and a top member 32 is connected to the proximal end of the section 30 with a gasket 34 between them. The gasket 34 has a central hole which allows the continuation of the interior wall 36 of the tubular section 22 to extend the full length of the cannula 10, as is best seen in FIG. 6. A second gasket 38 is disposed directly beneath the gasket 34. The gasket 38 has a pair of wall sections 40 and 42 at its center which act as a flap valve. In FIG. 6 the flap valve sections 40 and 42 illustrated in full line are shown closed and in dotted lines 44 are shown in an open position. The flap sections 44 are normally in the open position but when gas pressure is experienced on their distal side they are forced into the closed position of the full lines 40, 42.

As shown in FIG. 6, a pair of inclined suture cavities 48 and 50 are formed through the sections 26, 30 and 32. Their proximal ends open at the top of the section 32 and the lower ends of these passages 48 and 50 merge with the tubular interior 36 of the cannula at the distal end of the wall section 26. The passages 48 and 50 are adapted to receive two suture needles 16 which pass through the cannula 10 in the manner illustrated in the dotted lines in FIGS. 2, 4 and 6. The distal ends of the suture needles 16 pass through the side walls of the tubular section 22 of the cannula at a pair of slots in the side wall 52 and 54.

As is best seen in FIG. 7, the proximal passages 48 and 50 for the suture needles and the distal passages 52 and 54 are slightly separated laterally so that the two needles do not interfere with one another at the cross section 7-7 of FIG. 6.

The needles 16 are illustrated in detail in FIG. 8. The two suture needles are substantially identical. They each have a handle 66 at the proximal end and a cylindrical straight needle 68 having its proximal end within the handle 66 bearing against a compression spring 70. The compression spring biases the needle cylinder 68 toward an extended position from the handle. The lower end of the needle 68 has a blunt end 72 and a side slot 74 adapted to capture a suture. The outer side of the tubular inner member 68 is surrounded by a tubular sheath 76 which has its proximal end fixed with respect to the handle 66 in such a manner that it is not subjected to the biasing action of the spring 70. The distal end of the sheath 76 terminates in a sharpened cutting edge 78.

When the suture needle 16 is manually pressed downwardly against a resistive surface such as the tissue of the body cavity 12, the blunt end 72 forces the tube 68 to move upwardly within the handle compressing the spring 70 until the cutting tip 78 of the outer sheath 76 extends beyond the end 72 of the tube 68 and begins to penetrate the body tissue. When the cutting edge 78 has passed through the wall 12 into the body cavity 14, there is no longer any pressure on the end 72 and it extends beyond the cutting tip 78 under the spring bias, so that the cutting tip 78 will not contact the interior body organs.

FIG. 9 illustrates an alternative form for the end of the tube 68. Rather than having the edge configuration 74, a hole 82 connected to the bottom of the needle 68 by passage 84 is employed. The suture may be forced through the narrow neck of the passage 84 into the hole 82 to retain the suture.

FIG. 10 illustrates a preferred manner of performing an incision through the body wall 12 so that the cannula 10 may line the incision and act as a port for the insertion of various laparoscopic instruments such as endoscopes, surgical cutters, and the like.

Figure 11:
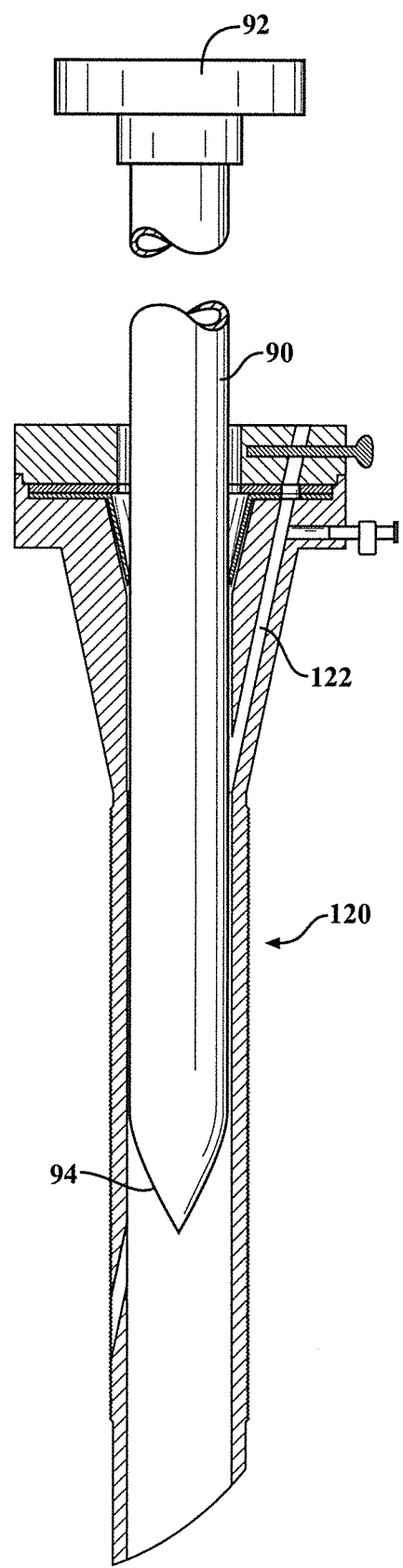
FIG. 11 is a cross-sectional view of a second embodiment of the cannula of the present invention with a trocar inserted into the barrel of the cannula.

The cannula generally indicated at 120 in FIG. 11 represents an alternative embodiment having only a single inclined passage 122 for a suture needle. Otherwise, it is the same as the two passage embodiment and is similarly numbered. Accordingly, after a suture has been introduced to the body cavity 14 through the single passage, it must be grasped by an instrument 112 introduced through a second port and freed from the needle. The cannula 120 is rotated by 90 degrees about its central axis within the incision. The instrument 112 then reattaches the suture to the needle and the needle and attached suture are withdrawn through the cannula and the two ends of the suture are knotted to close the incision.

To start the incision a surgeon will use a scalpel to make a small cut through the outer edge of the body wall 12 and then will bring the slanted end 20 of the cannula 10 or 120 into contact with the incision. A trocar 90 (FIG. 10) is then inserted through the central passage 36 of the cannula 10 or 120. The trocar has a handle 92 at its proximal end and a sharpened cutter 94 at its distal end. By pressure imposed on the handle 92, the trocar end 94 will be forced through the body wall to form the laparoscopic incision. When the trocar end 94 is passed into the body cavity 14, the cannula 10 or 120 is pressed down through the incision and the trocar is withdrawn.

The proximal ends of the two suture needle passages 48 and 50 in the cannula 10 are controlled by two valves 101 and 102. These valves may be pushbutton valves or rotatable valves and they may be moved between a position in which the passages 48 and 50 are closed and positions wherein they are open to allow the entry of suture needles 16. After the incision is made, with the valves 101 and 102 closed off, valve 106 which is connected to a source of inflating gas, preferably $CO_2$, is opened to feed $CO_2$ gas into the passage 50 leading to the interior volume 36 of the cannula 10 and into the body cavity 14. The $CO_2$ inflates the body cavity to enlarge its area and provide the surgeon with increased operating room. After the cavity 14 is filled and inflated, the valve 106 is closed off.

The cannula 10 is then ready for use as a port for the performance of a laparoscopic operation and various devices such as an endoscope, a surgical cutter, and the like may be passed through the port.

The surgeon will typically create one or more additional ports at spaced points on the outer surface of the body tissue so that various operations may be performed through certain of the ports under a physician's observation through an endoscope in an additional port.

After the laparoscopic operation is completed, it is necessary to suture the incisions used to form the ports. This is generally done in the sequence illustrated by FIGS. 1-5 using the two needle cannula. First, a suture 100 is connected to the distal end of a suture needle 16, one of the valves 101 or 102 is opened, and the needle is passed through that valve and through the interior of the cannula and out one of the exit ports 52 or 54, cutting passages through the body tissue on the distal side of the passages 52 or 54. This brings one end of the suture 110 into the body cavity 14 as illustrated in FIG. 2.

Next, as illustrated in FIG. 3, the free end of the suture is grasped by an instrument 112 which is introduced through another port (not shown) into the incision. The instrument 112 removes the suture from the end of the needle and the needle may then be withdrawn from the cannula and its entry valve closed, or it may be left within the cannula. Then, as illustrated in FIG. 4, a second needle, or the same one that inserted the suture into the body cavity, if it has been removed, is inserted into the cavity through the opposite inclined passage used for the first insertion. The instrument 112 is manipulated to engage the free end of the suture with the suture engaging formation either 74 or 82 at the end of this needle within the incision and, as shown in FIG. 5, the free end of the suture is pulled back through the passage occupied by the suture needle so that both free ends of the suture extend out of the proximal section 18 of the cannula. The cannula may then be removed and the suture knotted to close up the incision.

The cannula 10 may be removed from the incision at any time after the operation is completed. However, the insufflating gas pressure must be maintained so as to avoid having to re-inflate the operative site during surgery. Because the cannula 10 acts as a port from the initial step of incision through the completion of the surgery, it does not need to be removed until after suturing of the operative site has taken place. This keeps the body cavity insufflated and there will not be any need for re-insufflation.

Figure 12:
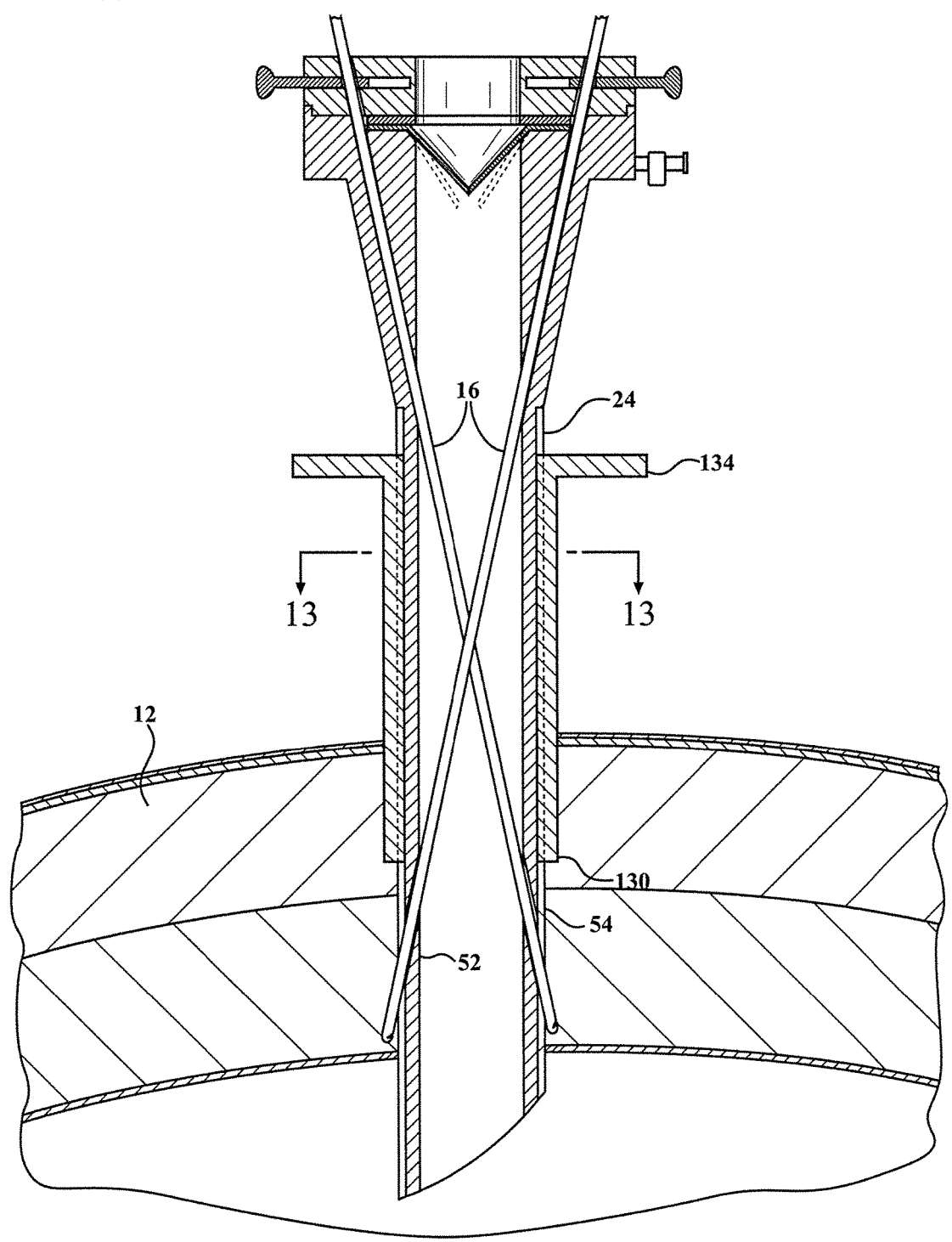
FIG. 12 is a sectional view of an alternative form of an aspect of the present invention with a blocking member in the form of a sliding sleeve to close the exit ports of the needle passages when they are not accommodating needles.

Another embodiment of the invention is illustrated in FIG. 12 which is directed toward avoiding the danger of the insufflating gas, which maintains the gas pressure in the body cavity during the procedure despite losses of the gas by being absorbed in the body tissue flowing out the ports 52 and 54 into the tissue of the cavity wall 12. This could cause subcutaneous emphysema or other undesirable effects. This is not a problem if the ports are within the body cavity 14, but is a danger if the needle outlet ports fall within the thickness of the body wall over the cavity.

Accordingly, a tubular blocking member sleeve 130 of a thin but rigid material, such as stainless steel or plastic, surrounds the lower section of the cannula wall 24. As disclosed in the cross section 13-13 through the blocking member sleeve 130 and the wall 24, shown in FIG. 13, in this embodiment the lower, tubular section of the cannula wall 24 is formed with a pair of longitudinal slots on diametrically opposed points. The tubular blocking member sleeve 130 is formed with complementary tongue members 132 that extend into the slots. Through a radially outward handle member 134 formed at the top of the sleeve 130, the blocking member sleeve may be manually moved by the surgeon between an upper position illustrated in FIG. 12, wherein its lower end is above the outlet ports 52 and 54 allowing the lower ends of the needles 16 to project out of the ports and a lowered position, illustrated in FIG. 14, in which the lower ends of the tube 130 block the exit ports so that the insufflation gases cannot penetrate the cavity wall 12. When the needles 16 project through the outlet ports 52 and 54, as illustrated in FIG. 12, they block the flow of insufflation gases through the ports. In a further embodiment, the blocking member sleeve is formed of a sheet of metal or plastic.

Figure 15:
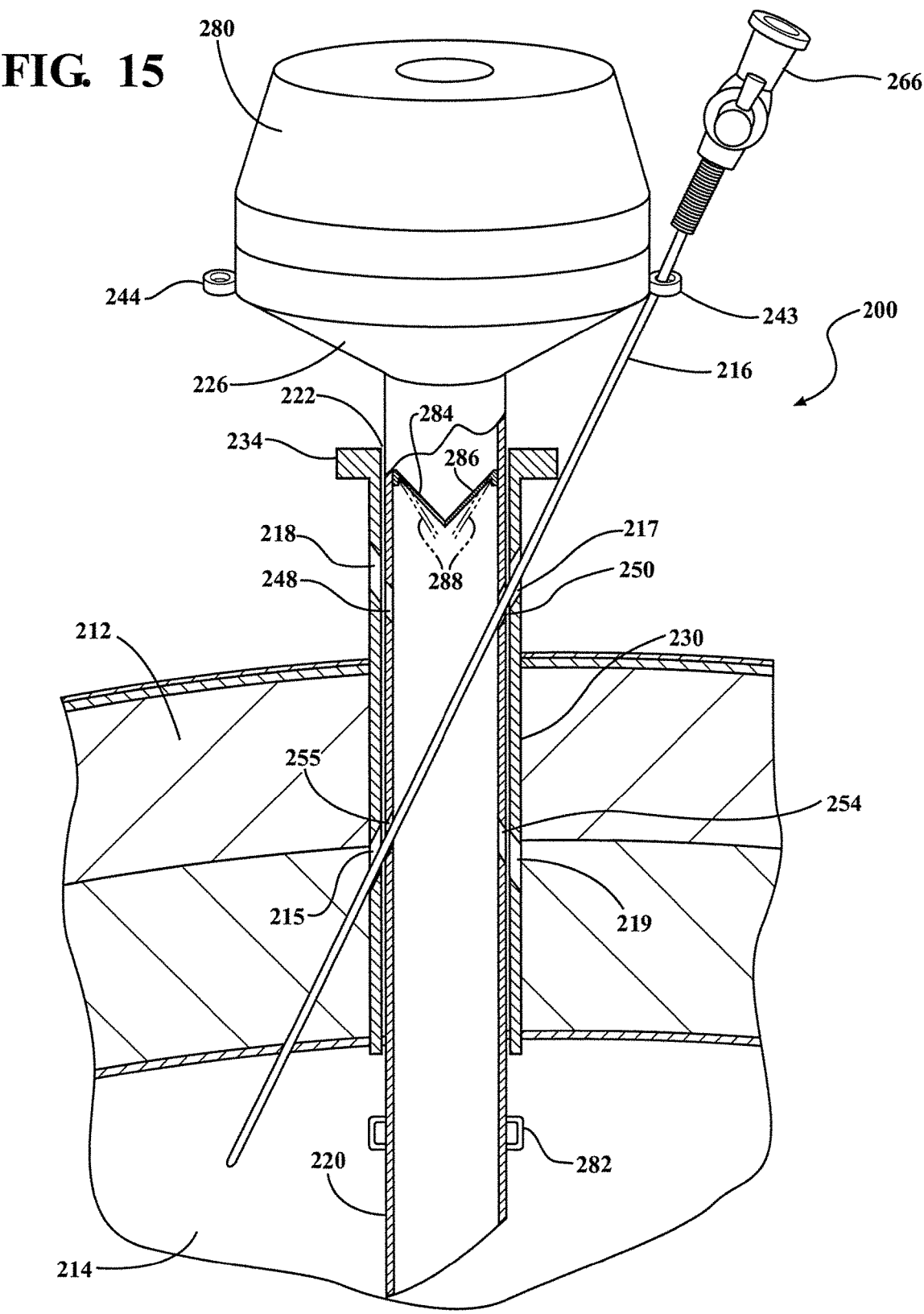
FIG. 15 is a partial cross-sectional view of a cannula of the present invention illustrating a pair of suture needle guides, the passages of a suture needle, a blocking member sleeve positioned to allow the suture needle to pass through the cannula into the body cavity and a protruding portion extending outwardly from the cannula to prevent the blocking member sleeve from moving further into the body cavity.
Figure 16:
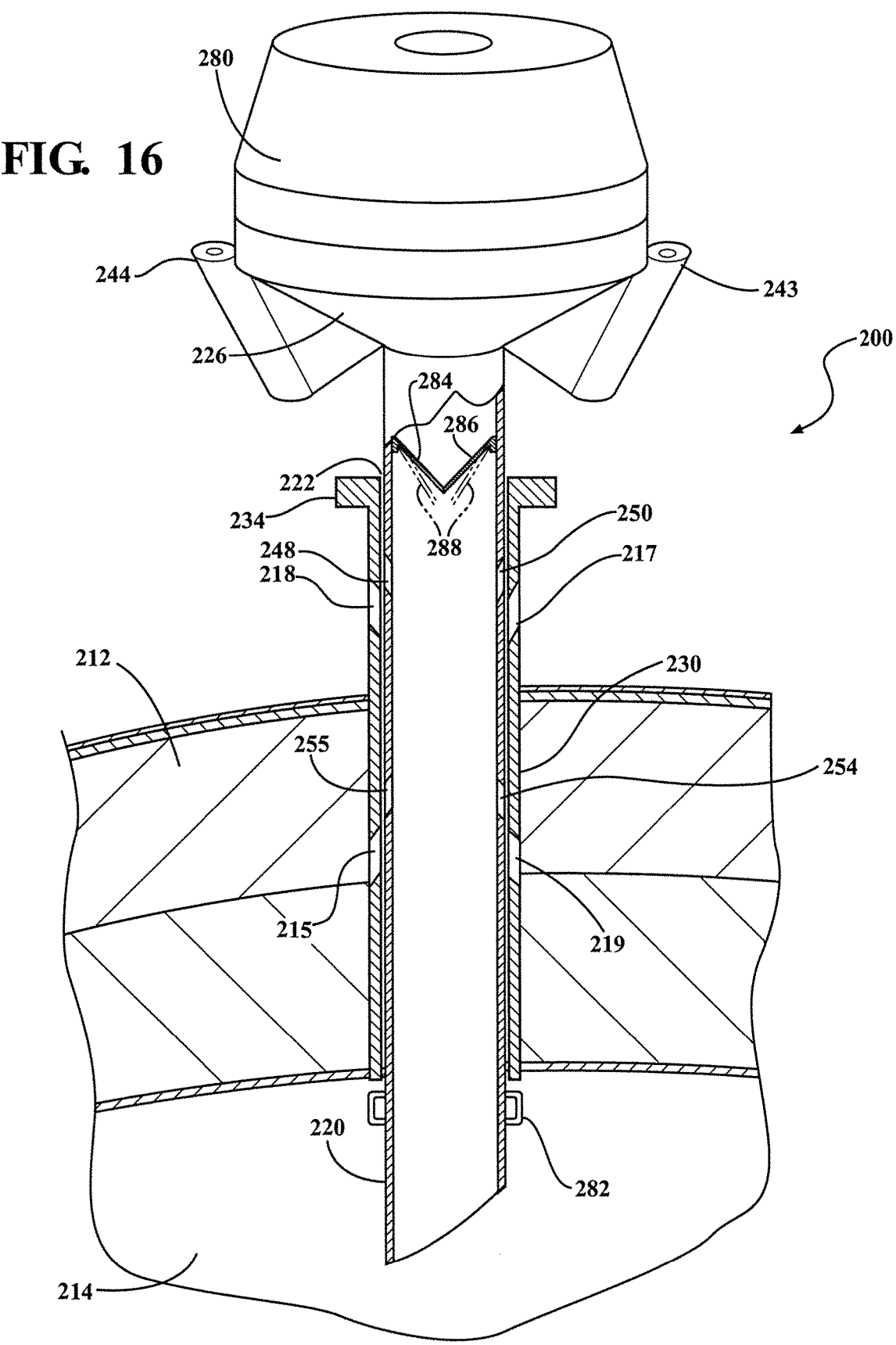
FIG. 16 is a partial cross-sectional view of a cannula of the present invention illustrating a pair of suture needle guides, the passages through which a suture needle would pass, a blocking member sleeve positioned by sliding longitudinally in parallel with the central axis of the cannula to block the suture needle from passing through the cannula into the body cavity and a protruding portion extending outwardly from the cannula to prevent the blocking member sleeve from moving further into the body cavity.
Figure 17:
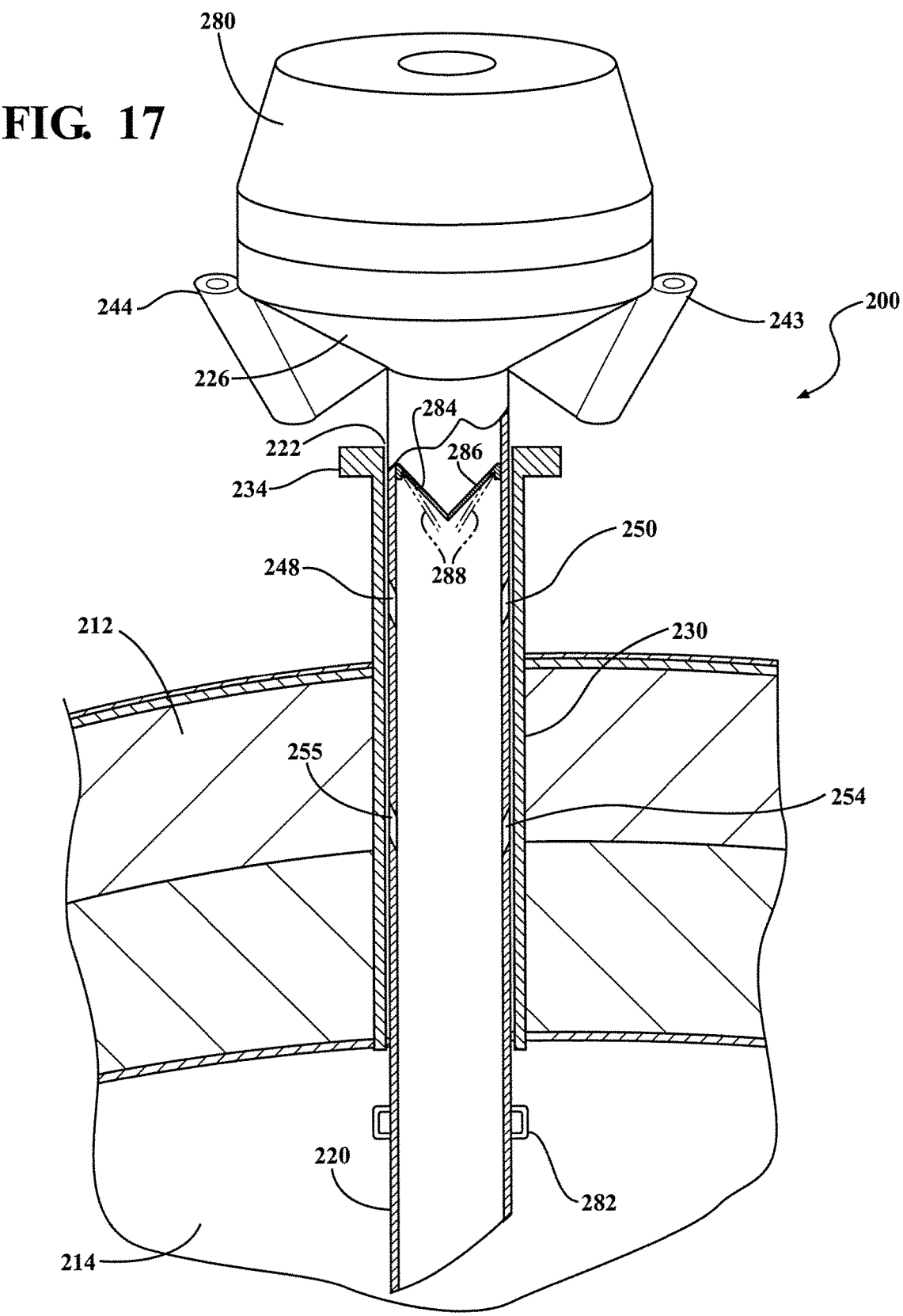
FIG. 17 is a partial cross-sectional view of a cannula of the present invention illustrating a pair of suture needle guides, the passages through which a suture needle would pass, a blocking member sleeve rotated to block the suture needle from passing through the cannula into the body cavity and a protruding portion extending outwardly from the cannula to prevent the blocking member sleeve from moving further into the body cavity.

FIGS. 15, 16 and 17 illustrate further embodiments of a cannula, generally indicated at 200, disposed in an operating position within a wall, generally indicated at 212, of a body cavity 214.

The cannula 200, illustrated in partial cross section in FIGS. 15, 16 and 17, includes an elongated tubular section 222 of somewhat greater length than the width of wall 212 of the body cavity 214 so the cannula extends through the wall 212 such that the proximal end 280 is external to the body and distal end 220 is disposed in the body cavity 214 in use. The elongated tubular section 222 of the cannula includes a cannula wall, is open at both its proximal and distal ends and has a central axis.

At the proximal end 280 of the cannula 200 the side walls of the cannula flare outwardly in a section 226 so that the width of the cannula on the proximal side of the tubular section 222 has a greater width than the balance of the tubular section.

As shown in FIGS. 15, 16 and 17, a pair of suture needle guides 243 and 244 is present at the periphery of the proximal end 280. The suture needle guide 243 allows passage of a suture needle and provides guidance and stability to the suture needle which then further passes through proximal and distal openings 250 and 255, respectively. The suture needle guide 244 allows passage of a suture needle and provides guidance and stability to the suture needle which then further passes through proximal and distal openings 248 and 254, respectively. A suture needle 216 is shown passing through the cannula 200 via the passage established through suture needle guide 243 and openings 250 and 255 in FIG. 15. A second suture needle can be used and would pass through the cannula 200 via the passage established through suture needle guide 244 and openings 248 and 254 in FIG. 15. The pair of suture needle guides are shaped to securely guide a suture needle and can have various shapes including ring-shaped as shown in FIG. 15 and gutter-shaped as shown in FIGS. 16 and 17. Similar to the configuration shown in FIGS. 6 and 7, the proximal passages 248 and 250 for the suture needles and the distal passages 255 and 254 are slightly separated laterally so that the two suture needles do not interfere with one another, see the cross section 7-7 of FIG. 6.

In this configuration, suture needles used optionally include a valve 266 for introduction or release of gas through the needle.

Shown in FIGS. 15, 16 and 17 is a tubular blocking member sleeve 230 of a thin but rigid material, such as stainless steel or plastic, surrounding a portion of the tubular section 222.

Figure 13:
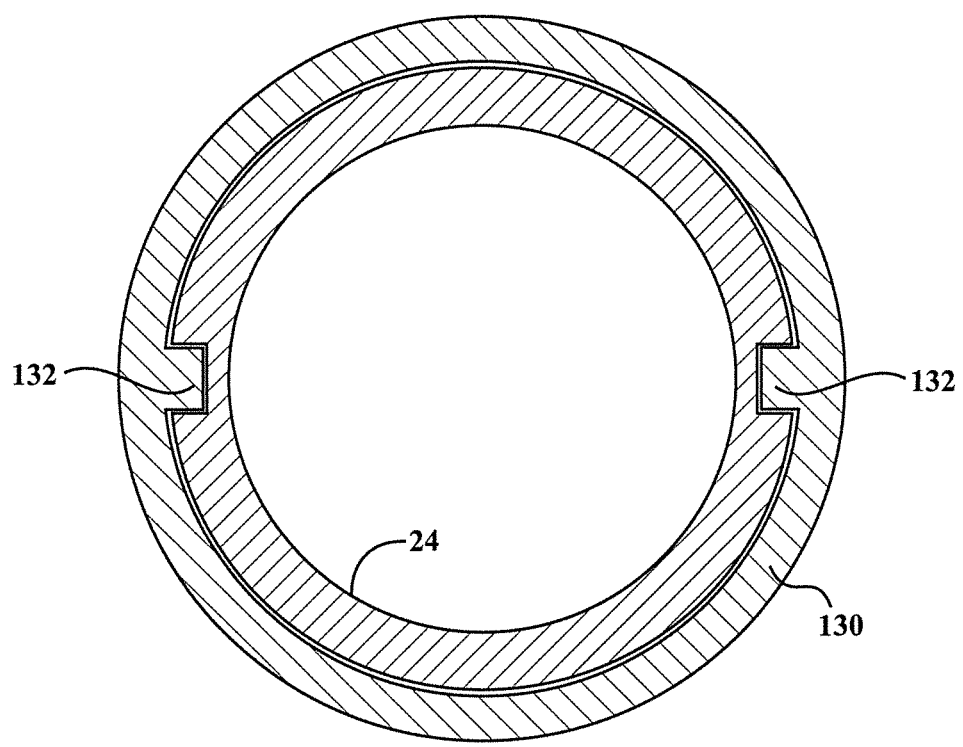
FIG. 13 is a section through the cannula and blocking member sleeve along section 13 of FIG. 12.
Figure 14:
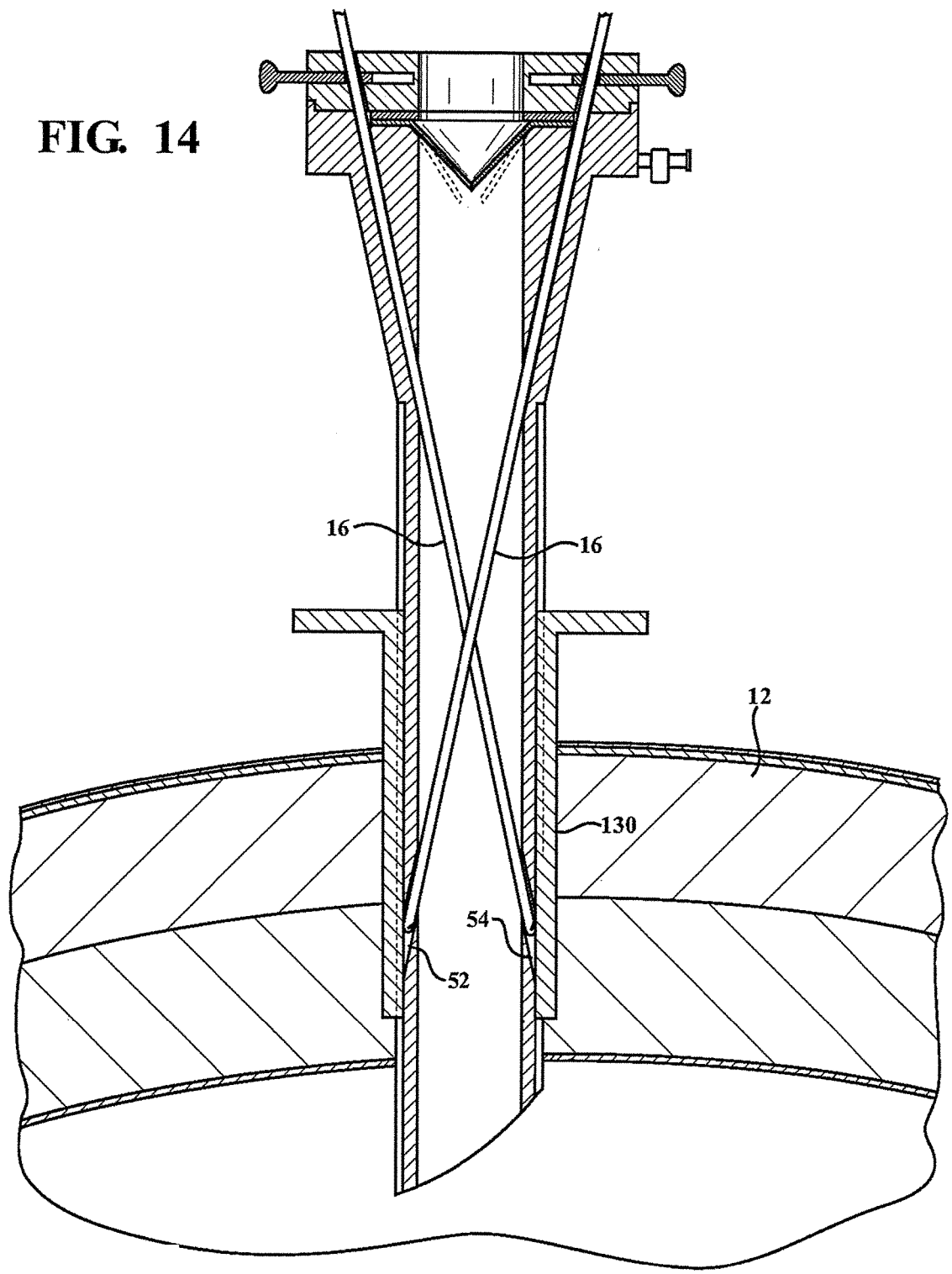
FIG. 14 is a view similar to FIG. 12 showing the blocking member sleeve blocking the exit ports of the needle passages.

Similar to the configuration in the cross section 13-13 of FIG. 12, shown in FIG. 13, a distal portion of the tubular section 222 is optionally formed with a pair of circumferentially offset longitudinal slots. According to this embodiment, the tubular blocking member sleeve 230 is formed with complementary tongue members that extend into the circumferentially offset longitudinal slots, guiding movement of the tubular blocking member sleeve along the exterior of tubular section 222 parallel to the central axis. The pair of circumferentially offset longitudinal slots is optionally located to be diametrically opposed to each other and the complementary tongue members of the tubular blocking member sleeve 230 would accordingly also be diametrically opposed to each other.

A handle member is optionally included on the tubular blocking member sleeve to move the tubular blocking member sleeve along the external surface of the tubular section of the cannula parallel to the central axis of the tubular section of the cannula and/or rotationally on the external surface of the tubular section of the cannula relative to the central axis of the tubular section of the cannula. The handle member extends outward from the proximal end of the tubular blocking member sleeve relative to the central axis of the tubular section of the cannula, such as radially outward. An outward extending handle member 234 formed at the top of the tubular blocking member sleeve 230, the tubular blocking member sleeve may be manually moved by the surgeon between 1) an upper position illustrated in FIG. 15, wherein the upper end of the sleeve is positioned such that sleeve ports 217 and 218 align with proximal openings 250 and 248, respectively and wherein the lower end of the sleeve is positioned such that sleeve ports 215 and 219 align with distal openings 255 and 254, respectively, allowing the lower ends of the suture needles 216 to project out of the openings and 2) a lower position, illustrated in FIG. 16, in which the sleeve 230 blocks the proximal openings 250 and 248 and distal openings 255 and 254 so that the insufflation gases cannot penetrate the body cavity wall 212. Note that when the suture needles 216 project through the proximal openings 250 and 248 and distal openings 255 and 254, as illustrated in FIG. 15, they block the flow of insufflation gases through the openings.

In a further option, the tubular blocking member sleeve 230 may be manually rotated by the surgeon between 1) an first position illustrated in FIG. 15, wherein the upper end of the sleeve is positioned such that sleeve ports 217 and 218 align with proximal openings 250 and 248, respectively and wherein the lower end of the sleeve is positioned such that sleeve ports 215 and 219 align with distal openings 255 and 254, respectively, allowing the lower ends of the suture needles 216 to project out of the openings and 2) a second position, illustrated in FIG. 17, in which the tubular blocking member sleeve 230 blocks the proximal openings 250 and 248 and distal openings 255 and 254 so that the insufflation gases cannot penetrate the body cavity wall 212.

A protruding portion 282 extends outwardly from distal end 220 of the cannula, preventing the tubular blocking member sleeve 230 from fully entering the body cavity 214 and potentially being lost therein. The protruding portion 282 can be a single element protruding from the distal end 220 of the cannula or multiple elements protruding from the distal end 220 of the cannula. According to aspects of the present invention, the protruding portion 282 can be a continuous single element encircling a portion of the distal end of the cannula.

According to aspects of the present invention, the extreme proximal end of the cannula 200 has walls extending laterally in a section 226 and a top member is connected to the proximal end of the section with a gasket between them, similar to the configuration shown in FIG. 6. The gasket has a pair of wall sections 284 and 286 at its center which act as a flap valve. In FIGS. 15-17 the flap valve sections 284 and 286 illustrated in full line are shown closed and in dotted lines 288 are shown in an open position. The flap sections 288 are normally in the open position but when gas pressure is experienced on their distal side they are forced into the closed position of the full lines 284 and 286.

Having thus disclosed my invention I claim:

1. A cannula for use in laparoscopic surgery performed through a wall of a body cavity, the cannula comprising:
   an elongated tubular section having a tubular section proximal end, a tubular section distal end, and a wall, the wall having an interior surface defining an interior of the tubular section and an exterior surface, the tubular section open at both the proximal and distal ends and having a central axis;
   a first passage through the wall of the tubular section and inclined with respect to the central axis, the first passage comprising a first opening through the wall of the tubular section at a position adjacent the proximal end of the tubular section, and a second opening through the wall of the tubular section adjacent to the distal end of the tubular section at a position on the wall circumferentially and distally offset compared to the position of the first opening, the first and second openings being aligned so that a first straight suture needle having a proximal end and a distal end may be passed through both the first and second openings with a section of the first straight suture needle intermediate the first and second openings transversing the interior of the tubular section at an angle of inclination to said central axis, and with the distal end of the first straight suture needle projecting out of the second opening and into a body cavity;
   a first suture needle guide disposed at or near the tubular section proximal end of the elongated tubular section on the exterior surface of the wall at an external periphery of the tubular section proximal end such that the first suture needle guide laterally and externally extends from the exterior surface of the wall and is spaced away from the interior surface of the wall, where the first suture needle guide is a ring, the first suture needle guide being aligned so that the first straight suture needle may be passed through the first suture needle guide and both the first and second openings with the section of the first straight suture needle intermediate the first and second openings transversing the interior of the tubular section at an angle to said central axis, and with the distal end of the first straight suture needle projecting out of the second opening and into the body cavity; and
   a blocking member slidably supported on the elongated tubular section for motion along or around the central axis on said exterior surface of the wall between a first position in which the blocking member blocks flow of gases through said first and second openings and a second position clear of said first and second openings for allowing passage of said first straight suture needle through said first and second openings.

2. The cannula of claim 1, wherein said blocking member comprises a tubular sleeve surrounding or partially surrounding the tubular section of the cannula.

3. The cannula of claim 2, where the blocking member is formed of a sheet of metal.

4. The cannula of claim 2, where the blocking member is formed of sheet plastic.

5. The cannula of claim 1, wherein the blocking member carries a projection extending outward relative to the central axis for use in movement of the blocking member between the first and second positions.

6. The cannula of claim 1, wherein a pair of grooves extend parallel to said central axis on diametrically opposed sections of the exterior surface of the tubular section and the blocking member comprises a pair of inward radially extending tongue members adapted to ride in said grooves.

7. The cannula of claim 1, further including a second passage through the wall of the tubular section at a position circumferentially offset to the first passage, the second passage being inclined with respect to the central axis of the tubular section at an angle complementary to the angle of inclination of the first passage so that extensions of the first and second passages cross one another in the center of the tubular section, the second passage comprising a third opening through the wall of the tubular section adjacent the proximal end of the tubular section at a position on the wall circumferentially offset to the first opening, and a fourth opening through the wall of the tubular section adjacent to the distal end of the tubular section at a position on the wall circumferentially offset compared to the position of the second opening, the third and fourth openings being aligned so that a second straight suture needle having a proximal end and a distal end may be passed through both the third and fourth openings with a section of the second straight suture needle intermediate the third and fourth openings transversing the interior of the tubular section at an angle to said central axis, and with the distal end of the second straight suture needle projecting out of the fourth opening and into the body cavity;
- a second suture needle guide disposed at or near the proximal end of the elongated tubular section and circumferentially offset to the first suture needle guide, the second suture needle guide being aligned so that the second straight suture needle may be passed through the second suture needle guide and both the third and fourth openings with the section of the second straight suture needle intermediate the third and fourth openings transversing the interior of the tubular section at an angle to said central axis, and with the distal end of the second straight suture needle projecting out of the fourth opening and into the body cavity; and
- wherein the blocking member is slidably supported on the elongated tubular section for motion along or around the central axis on said exterior surface of the wall between the first position in which the blocking member blocks flow of gases through all of said first, second, third and fourth openings and the second position clear of all of said first, second, third and fourth openings for allowing passage of said first straight suture needle through said first and second opening and said second straight suture needle through said third and fourth openings.

8. The cannula of claim 1, wherein the second opening through the wall of the tubular section adjacent to the distal end of the tubular section is at a position on the wall diametrically opposed and distally offset compared to the position of the first opening.

9. The cannula of claim 1, further comprising a protruding portion, the protruding portion extending outward relative to the central axis from the distal end of the tubular section for preventing the blocking member from fully entering the body cavity.

10. A cannula for use in laparoscopic surgery performed through a wall of a body cavity, the cannula comprising:
- an elongated tubular section having a tubular section proximal end, a tubular section distal end, and a wall, the wall having an interior surface defining an interior of the tubular section and an exterior surface, the tubular section open at both the proximal and distal ends and having a central axis;
- a first passage through the wall of the tubular section and inclined with respect to the central axis, the first passage comprising a first opening through the wall of the tubular section at a position adjacent the proximal end of the tubular section, and a second opening through the wall of the tubular section adjacent to the distal end of the tubular section at a position on the wall circumferentially and distally offset compared to the position of the first opening, the first and second openings being aligned so that a first straight suture needle having a proximal end and a distal end may be passed through both the first and second openings with a section of the first straight suture needle intermediate the first and second openings transversing the interior of the tubular section at an angle of inclination to said central axis, and with the distal end of the first straight suture needle projecting out of the second opening and into a body cavity;
- a first suture needle guide disposed at or near the tubular section proximal end of the elongated tubular section on the exterior surface of the wall at an external periphery of the tubular section proximal end such that the first suture needle guide laterally and externally extends from the exterior surface of the wall and is spaced away from the interior surface of the wall, where the first suture needle guide comprises a tube, the first suture needle guide being aligned so that the first straight suture needle may be passed through the first suture needle guide and both the first and second openings with the section of the first straight suture needle intermediate the first and second openings transversing the interior of the tubular section at an angle to said central axis, and with the distal end of the first straight suture needle projecting out of the second opening and into the body cavity; and
- a blocking member slidably supported on the elongated tubular section for motion along or around the central axis on said exterior surface of the wall between a first position in which the blocking member blocks flow of gases through said first and second openings and a second position clear of said first and second openings for allowing passage of said first straight suture needle through said first and second openings.

11. The cannula of claim 10, wherein said blocking member comprises a tubular sleeve surrounding or partially surrounding the tubular section of the cannula.

12. The cannula of claim 10, wherein the blocking member carries a projection extending outward relative to the central axis for use in movement of the blocking member between the first and second positions.

13. The cannula of claim 10, wherein a pair of grooves extend parallel to said central axis on diametrically opposed sections of the exterior surface of the tubular section and the blocking member comprises a pair of inward radially extending tongue members adapted to ride in said grooves.

14. The cannula of claim 10, wherein the second opening through the wall of the tubular section adjacent to the distal end of the tubular section is at a position on the wall diametrically opposed and distally offset compared to the position of the first opening.

15. The cannula of claim 10, further comprising a protruding portion, the protruding portion extending outward relative to the central axis from the distal end of the tubular section for preventing the blocking member from fully entering the body cavity.

16. A cannula for use in laparoscopic surgery performed through a wall of a body cavity, the cannula comprising:
- an elongated tubular section having a tubular section proximal end, a tubular section distal end, and a wall, the wall having an interior surface defining an interior of the tubular section and an exterior surface, the tubular section open at both the proximal and distal ends and having a central axis;
- a first passage through the wall of the tubular section and inclined with respect to the central axis, the first passage comprising a first opening through the wall of the tubular section at a position adjacent the proximal end of the tubular section, and a second opening through the wall of the tubular section adjacent to the distal end of the tubular section at a position on the wall circumferentially and distally offset compared to the position of the first opening, the first and second openings being aligned so that a first straight suture needle having a proximal end and a distal end may be passed through both the first and second openings with a section of the first straight suture needle intermediate the first and second openings transversing the interior of the tubular section at an angle of inclination to said central axis, and with the distal end of the first straight suture needle projecting out of the second opening and into a body cavity;

a first suture needle guide disposed at or near the tubular section proximal end of the elongated tubular section on the exterior surface of the wall at an external periphery of the tubular section proximal end such that the first suture needle guide laterally and externally extends from the exterior surface of the wall and is spaced away from the interior surface of the wall, the first suture needle guide being aligned so that the first straight suture needle may be passed through the first suture needle guide and both the first and second openings with the section of the first straight suture needle intermediate the first and second openings transversing the interior of the tubular section at an angle to said central axis, and with the distal end of the first straight suture needle projecting out of the second opening and into the body cavity;

a blocking member slidably supported on the elongated tubular section for motion along or around the central axis on said exterior surface of the wall between a first position in which the blocking member blocks flow of gases through said first and second openings and a second position clear of said first and second openings for allowing passage of said first straight suture needle through said first and second openings; and a protruding portion, the protruding portion extending outward relative to the central axis from the distal end of the tubular section for preventing the blocking member from fully entering the body cavity.

17. The cannula of claim 16, wherein said blocking member comprises a tubular sleeve surrounding or partially surrounding the tubular section of the cannula.

18. The cannula of claim 16, wherein the blocking member carries a projection extending outward relative to the central axis for use in movement of the blocking member between the first and second positions.

19. The cannula of claim 16, wherein a pair of grooves extend parallel to said central axis on diametrically opposed sections of the exterior surface of the tubular section and the blocking member comprises a pair of inward radially extending tongue members adapted to ride in said grooves.

20. The cannula of claim 16, wherein the second opening through the wall of the tubular section adjacent to the distal end of the tubular section is at a position on the wall diametrically opposed and distally offset compared to the position of the first opening.

* * * * *